(12) United States Patent
Neuberger

(10) Patent No.: US 7,331,983 B2
(45) Date of Patent: *Feb. 19, 2008

(54) FIBER ASSISTED IRRADIATION SYSTEM AND METHOD FOR BIOSTIMULATION

(75) Inventor: Wolfgang Neuberger, Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 237 days.

This patent is subject to a terminal disclaimer.

(21) Appl. No.: 10/617,917

(22) Filed: Jul. 10, 2003

(65) Prior Publication Data

US 2004/0078068 A1    Apr. 22, 2004

Related U.S. Application Data

(62) Division of application No. 09/931,341, filed on Aug. 16, 2001, now Pat. No. 6,830,580.

(51) Int. Cl.
*A61N 5/06* (2006.01)

(52) U.S. Cl. .............................. 607/89; 606/10; 606/13; 128/898

(58) Field of Classification Search ............ 607/88–93; 385/32, 901; 128/898; 606/10–13
See application file for complete search history.

(56) References Cited

U.S. PATENT DOCUMENTS

| | | | |
|---|---|---|---|
| 4,612,604 A | | 9/1986 | Schlyter |
| 4,686,986 A | | 8/1987 | Fenyo et al. |
| 4,761,047 A | * | 8/1988 | Mori ........................... 607/88 |
| 4,907,132 A | * | 3/1990 | Parker ......................... 385/32 |
| 4,930,504 A | * | 6/1990 | Diamantopoulos et al. ... 607/88 |
| 5,021,452 A | | 6/1991 | Labbe et al. |
| 5,175,785 A | * | 12/1992 | Dabby ........................ 385/123 |
| 5,344,433 A | | 9/1994 | Talmore |
| 5,616,140 A | | 4/1997 | Prescott |
| 5,755,752 A | | 5/1998 | Segal |
| 6,084,242 A | | 7/2000 | Brown, Jr. et al. |
| 6,156,028 A | * | 12/2000 | Prescott ....................... 607/88 |
| 6,663,659 B2 | * | 12/2003 | McDaniel .................... 607/88 |

* cited by examiner

*Primary Examiner*—David M. Shay
(74) *Attorney, Agent, or Firm*—B J Associates; Bolesh J. Skutnik

(57) ABSTRACT

The present invention provides a system and method for improved biostimulative effect through the use of low mode/oligomode fibers to transport coherent light to a treatment site. Oligomode fibers or groups/bundles of oligomode waveguides for the relevant irradiation wavelength are used for radiation transport. Selective leakage of the radiation from this delivery system is achieved at the desired application sites of the biostimulation by suitable means, one being evanescent wave decouplers. The result is a low intensity exposure of coherent light to tissue or organic material that is more effective than conventional biostimulative procedures. Delivery systems based on such waveguides can cover large areas due to the low transmission losses of the waveguide. The waveguide can be inserted into hydrocultures or earth to provide radiation and thus biostimulation of seeds and cuttings in situ. Coherent radiation can also improve the health, healing and fertility of animals.

8 Claims, 5 Drawing Sheets

FIBER ASSISTED IRRADIATION SYSTEM AND METHOD FOR BIOSTIMULATION

REFERENCE TO RELATED CASE

This application is a divisional of U.S. patent application Ser. No. 09/931,341 filed on Aug. 16, 2001 now U.S. Pat. No. 6,830,580 by Wolfgang Neuberger, inventor, entitled "Fiber Assisted Irradiation System and Method for Biostimulation", and incorporated by reference herein.

BACKGROUND OF THE INVENTION

1. Field of the Invention

The present invention relates to the field of biostimulation devices and in particular a device and method to increase the efficiency of the biostimulative effect.

2. Invention Disclosure Statement

Biostimulation is the exposure of organic tissue such as plant, animals, bacteria or specific cells to low levels of radiation. Once exposed these tissues exhibit increased levels of biological activity. Plant growth is accelerated following the irradiation of seeds or cuttings. Decreases in the accumulation of harmful heavy metals and increases in beneficial elements such as Selenium have been reported. Increased fertility can occur in some animals treated with biostimulation. The effects reported are strongly dependent on the radiation dosage applied as well as the range of the wavelength used. Devices and methods for the most effective use of application of the biostimulation have generally been ignored.

U.S. Pat. No. 4,612,604 describes an invention that utilizes polarized light for biostimulation purposes. This patent describes a device that creates a large area of polarized light for biostimulative treatment. Exposure to polarized light has some biostimulative effect and the invention has the ability to affect a large area. The invention does not reveal the use of coherent light and the light used contains many modes.

U.S. Pat. No. 4,686,986 describes a method and apparatus for promoting healing of lesions through irradiation with polarized light. Exposure of the lesion to polarized light leads to some increase in the rate of healing. In the described invention only noncoherent light in wavelengths greater than 300 nm is employed.

U.S. Pat. No. 4,930,504 describes a device for biostimulation. The device utilizes an array of substantially monochromatic radiation sources; preferably laser diodes, having a plurality of wavelengths to treat an area of tissue. The invention does not reveal an application for coherent light at treatment sites or the benefits of using a coherent light source.

U.S. Pat. No. 5,021,452 describes a process for accelerating wound healing by exposure to laser light of wavelengths between 600 nm and 1000 nm combined with the application of ascorbic acid. Exposure of cells to these wavelengths of light increases the intake of ascorbic acid into the cell. Ascorbic acid increases cross-linking in may intracellular protein structures which leads to increased healing. The described invention does not reveal how to increase the efficiency of each wavelength of light used or how to increase the efficacy of the biostimulative effect through the use of coherent light.

U.S. Pat. No. 5,344,433 describes a device that uses a physically narrow beam of light transported by a light guide to treat skin wounds such as psoriasis or other lesions of the skin. This invention utilizes a high intensity source creating an illumination of at least 1 mW per $cm^2$. The light source used here is an arc lamp, which again is a non-coherent source of light.

U.S. Pat. No. 5,616,140 describes an invention that uses laser diodes to accelerate wound healing. These diodes are incorporated into bandages or various pieces of clothing such that a constant level of low power beam energy can be applied to the treatment areas. The effect of this constant exposure to low level energy is the acceleration of the healing process. This patent does not reveal the application or advantages of using coherent light and does not reveal an application of single or limited mode fibers. The invention also requires multiple diodes to cover most areas and does not reveal how to treat a large area with just a single light source.

U.S. Pat. No. 5,755,752 describes a device that controls the amount of radiation exposure, which can occur during biostimulative therapy. The radiation source is contained within a wand form. This allows the user to physically control the application of the radiation source. This physical control requires that the user move the wand from location to location for each desired treatment site. This patent does not reveal how to affect more than a single site simultaneously.

U.S. Pat. No. 6,084,242 describes an invention that utilizes electromagnetic radiation of about 1800-2040 nm to stimulate the human immune system. Specifically, the described invention uses a wavelength of 1917 nm at a pulse rate of about 7.5 Hz to treat various cancers. Exposure to infrared radiation is shown to stimulate a body's own immune system to attack the cancerous cells. The described invention uses light that is not coherent radiation as the phrase is used with respect to laser technology but is derived from a laser source via circuitry. The invention does not describe the benefits of using coherent light to enhance the biostimulative effect.

It would be useful to have a method for biostimulation that efficiently uses substantially coherent light, which is versatile in its broad area application, as well as narrow exposure to any organic tissue. More specifically, a useful application of the biostimulative effect would be one that is applicable to large areas on the human body as well as large areas like farmland. It would be further useful if the biostimulation effect could be performed to effect tissue or organic matter below the surface of the skin or land. The current invention describes highly effective and efficient radiation delivery means and treatment modalities characterized in particular by their maintaining a high degree of coherence of the laser sources used.

OBJECTIVES AND BRIEF SUMMARY OF THE INVENTION

It is an object of the present invention to provide a device for improved biostimulative effect utilizing coherent light.

It is another object of the present invention to provide a system that transmits the light emitted from a coherent light source via oligomode fibers.

It is a further object of the present invention to provide a biostimulative device that uses coherent light, transported via single mode fibers that can utilize evanescent wave extraction as a means to expose treatment areas to the light.

Briefly stated, the present invention provides a system and method for improved biostimulative effect through the use of low mode/oligomode fibers to transport coherent light to a treatment site. Oligomode fibers or groups/bundles of oligomode waveguides for the relevant irradiation wavelength are used for radiation transport. Selective leakage of the radiation from this delivery system is achieved at the desired application sites of the biostimulation by suitable means, one being evanescent wave decouplers. The result is a low intensity exposure of coherent light to tissue or organic material that is more effective than conventional biostimulative procedures. Delivery systems based on such waveguides can cover large areas due to the low transmission losses of the waveguide. The waveguide can be inserted into hydrocultures or earth to provide radiation and thus biostimulation of seeds and cuttings in situ. Coherent radiation can also improve the health, healing and fertility of animals.

The above, and other objects, features and advantages of the present invention will become apparent from the following description read in conjunction with the accompanying drawings, (in which like reference numbers in different drawings designate the same elements.)

BRIEF DESCRIPTION OF FIGURES

FIG. 3b depicts a lateral cross-section of FIG. 3a.

DETAILED DESCRIPTION OF PREFERRED EMBODIMENTS

Figure 1:
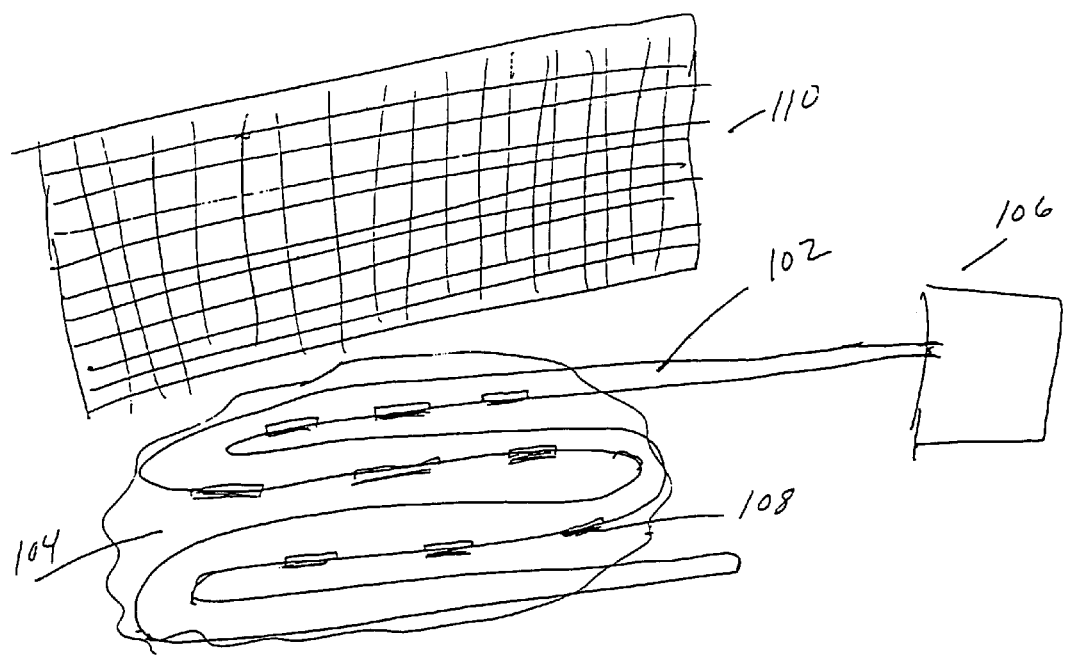
FIG. 1 illustrates an oligomode waveguide used to treat a wound

Biostimulation can be performed in many ways on a number of organic tissues. Generally, a light source is filtered such that a certain wavelength or range of wavelengths is transmitted. Tissue is then exposed to the filtered light. It has been shown that biostimulation is particularly effective in dark environments. For example, the irradiation of certain bacteria and other organisms in the soil can be achieved in the vicinity of roots to promote growth.

It is possible by biostimulation to increase the effects of certain hormones or other bioactive elements and thereby lower the dosages required. The irradiation system and approach of the present invention can control the administration of desirable elements by controlling the timing sequence between the injection of certain bioactive elements and delivery of the irradiation stimulation.

It has been found that coherent (laser) radiation is more effective in biostimulation than equivalent radiation dosage obtained from an incoherent but monochromatic source, such as a lamp with suitable filters. While the precise reasons for the effect is not well understood, its implications have been neglected by today's biostimulation system designs and methods. Virtually all irradiation of seedling or cuttings has been carried out with free beam systems on the samples prior to being planted. In the biostimulation of wounds or other sites in humans or animals either free beam irradiation or large diameter light guides have typically been used.

It is felt that at least a part of the shortcomings of the biostimulation approach and some inconsistencies in the reported effects can be explained by the general need for sophisticated and devoted attention to the delivery system. In particular, no attention has been paid so far to the benefits of maintaining coherence in the transmission system or to the effectiveness of the whole biostimulation process in terms of its economics, ease of use and consistency.

The individual waveguides of the present invention typically have core diameters of several micrometers. The exact dimensions will depend on the wavelength chosen for the application. Radiation from Argon (Ar) lasers, Helium-Neon (HeNe) lasers at 630 nm and similar wavelength diode lasers has proven useful. The cladding on these waveguides serves to protect the core fiber and enhance performance. The use of oligomode, or low mode, fibers permits radiation waves to travel great lengths through the fibers and allows radiation sources to be kept significant distances from the biostimulation sites. While fully coherent radiation appears ideal for biostimulation, biostimulation effects can also be achieved with somewhat less perfect sources. Therefore, less than perfect transmission and radiation delivery means should be considered within the scope of the present invention. It is possible to use fiber optics or waveguides and sources with a limited number of modes in the system, sometimes called oligomode fibers, and still achieve good biostimulation results. This can help to achieve the required irradiation levels of several Watts per square meter for 60 second durations and the 2 to 3 irradiation cycles typically required.

Oligomode fibers are known in the art and are also commonly referred to as low mode fibers, in that they are able to support only a limited number of modes, in contrast to single mode fibers that support only one mode, or possibly two modes, and also in contrast to multi-mode fibers which typically have a diameter of at least 50 microns and can support thousands of modes. The number of modes a fiber can support depends on its core diameter, numerical aperture, and the wavelength used.

Oligomode fibers are preferable in some instances of the present invention due to the fact that single mode fibers have very small core diameters (typically less than 10 microns) and relatively large cladding thicknesses, which impede the selective out-coupling of radiation without compromising the strength of the fiber. It is preferable in some instances to have a thicker core to facilitate leakage. A thicker core necessarily means more transmission modes and therefore less coherence, but there is a range where less than perfect coherence remains acceptable. Known formulas can be used to calculate the maximum number of modes that can be accommodated in a fiber with a given core diameter and NA value.

As the required diameter changes with every treatment and every fiber, there is not a single limit to the number of modes, although the number of modes would be on the order of 10's and possibly 100's in contrast to the thousands of modes present in a typical multi-mode fiber. The characteristics of optical fibers as described above are well known by those skilled in the art.

Although evanescent wave decouplers are the preferred method to leak radiation from the optical fibers of this invention, other techniques known to those skilled in the art are also incorporated herein. The include, but are not limited to gratings, reflective layers, and modifications of the core or cladding by laser ablation, chemical etching, ion implantation, and addition of chemical dopants.

The present invention is further illustrated by the following examples, but is not limited thereby.

EXAMPLE 1

Referring to FIG. 1, a length of oligomode fiber 102 is used to treat a large area of lesions 104. Fiber 102 is laid across area of lesions 104 in a serpentine fashion. Single mode fiber 102 is attached to suitable light source 106 for wound healing. At suitable intervals for a desired treatment evanescent wave decouplers 108 are positioned. The fiber can be laid on the wound and covered with dressing 110. This allows for a constant low-level biostimulation that the patient can take with him, instead of large doses of treatment at longer or irregular intervals.

EXAMPLE 2

Figure 2:
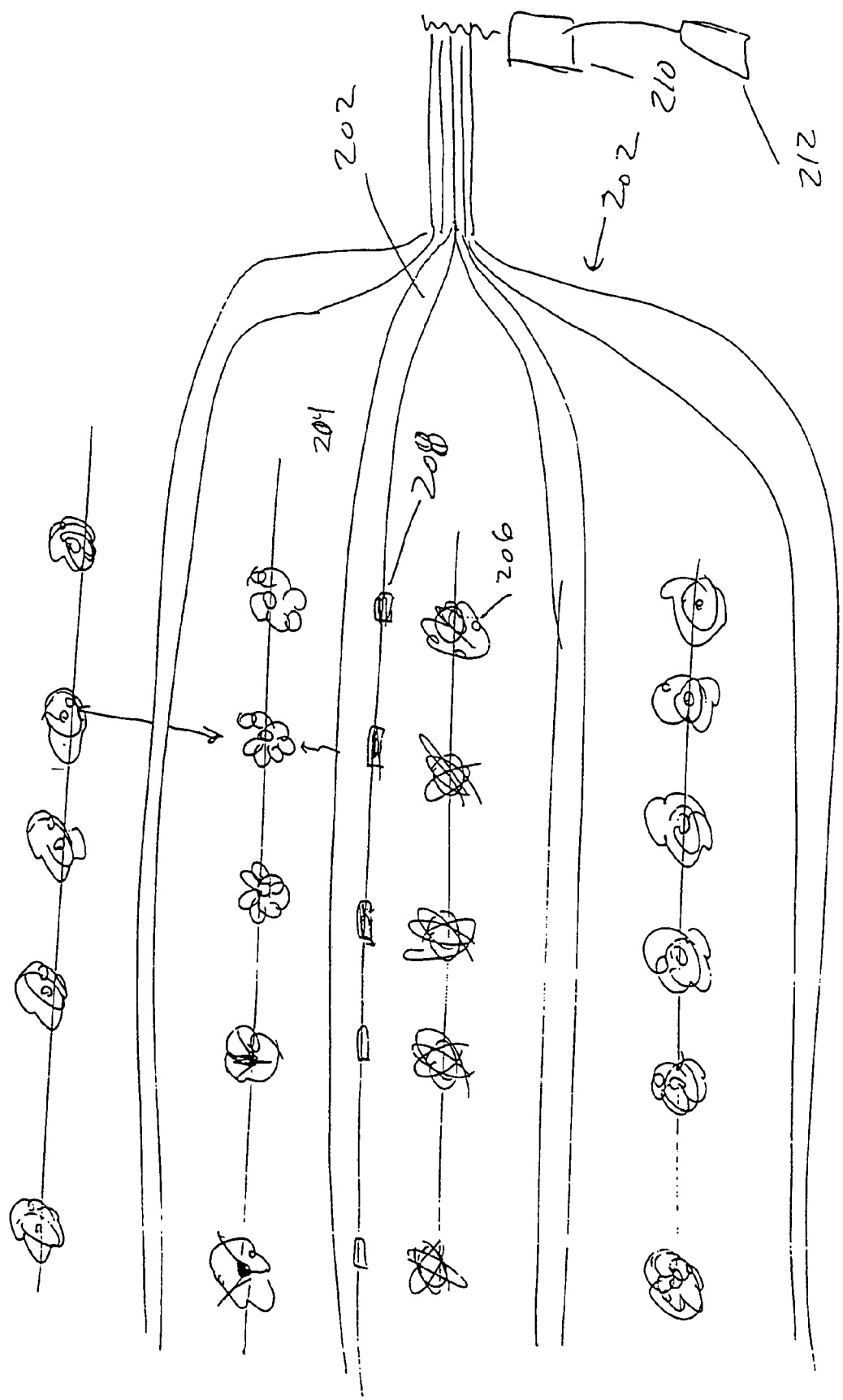
FIG. 2 illustrates a collection of single waveguides having a common light source, positioned in an agricultural filed.

Referring to FIG. 2, a large length of oligomode fiber optic waveguide 202 has evanescent wave decouplers 208 placed along its length at a desired seeding interval laid into the ground 204 along with seeds 206 at planting. At each seeding interval a corresponding evanescent wave decoupler 208 is positioned to allow biostimulation of adjacent seeds. Light source 210 transmits coherent light through waveguide 202. Light source 210 may be intermittently controlled by timer mechanism 212 or operated at constant level.

EXAMPLE 3

Figure 3A:
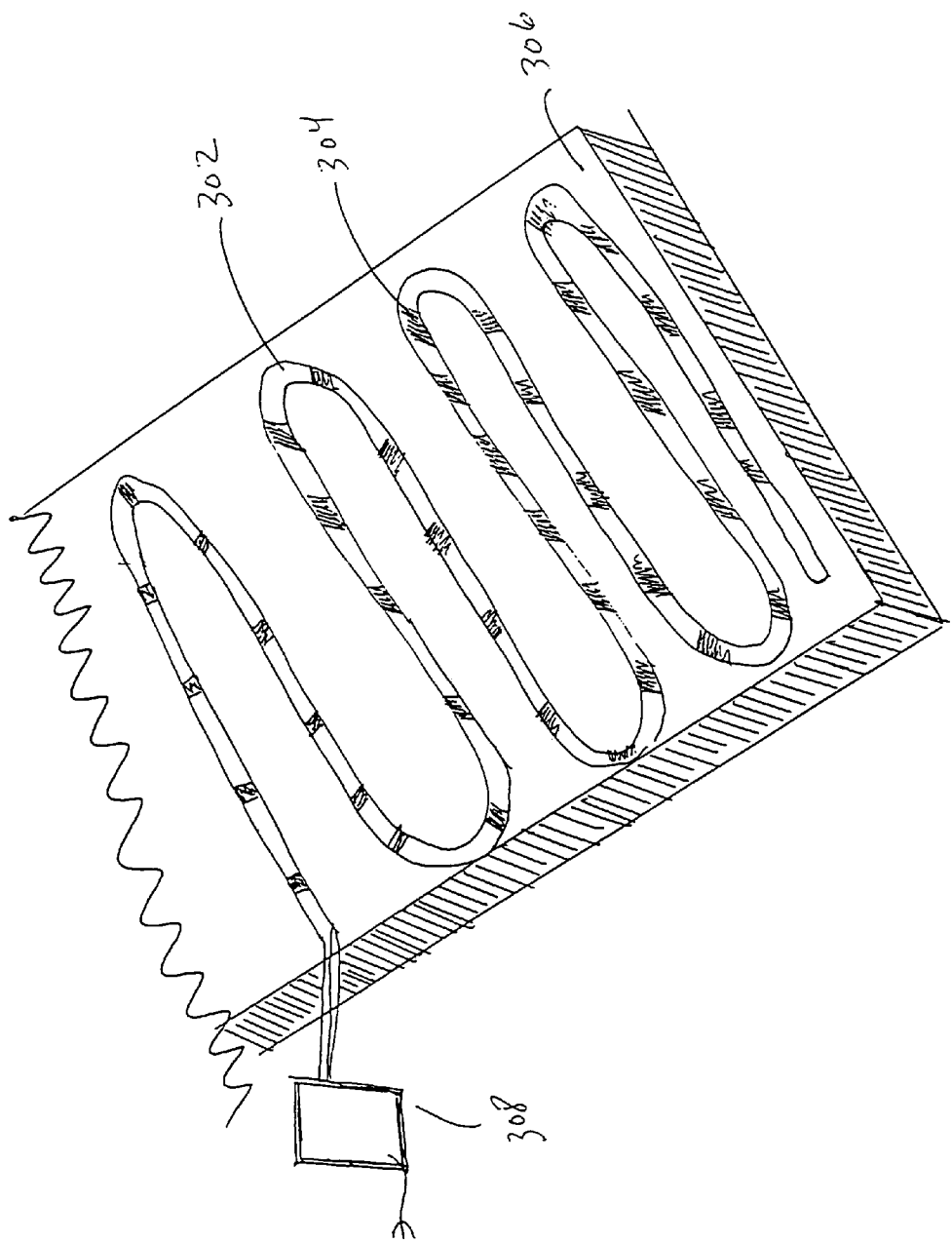
FIG. 3a illustrates a single waveguide continuously recessed in a floor.
Figure 3B:
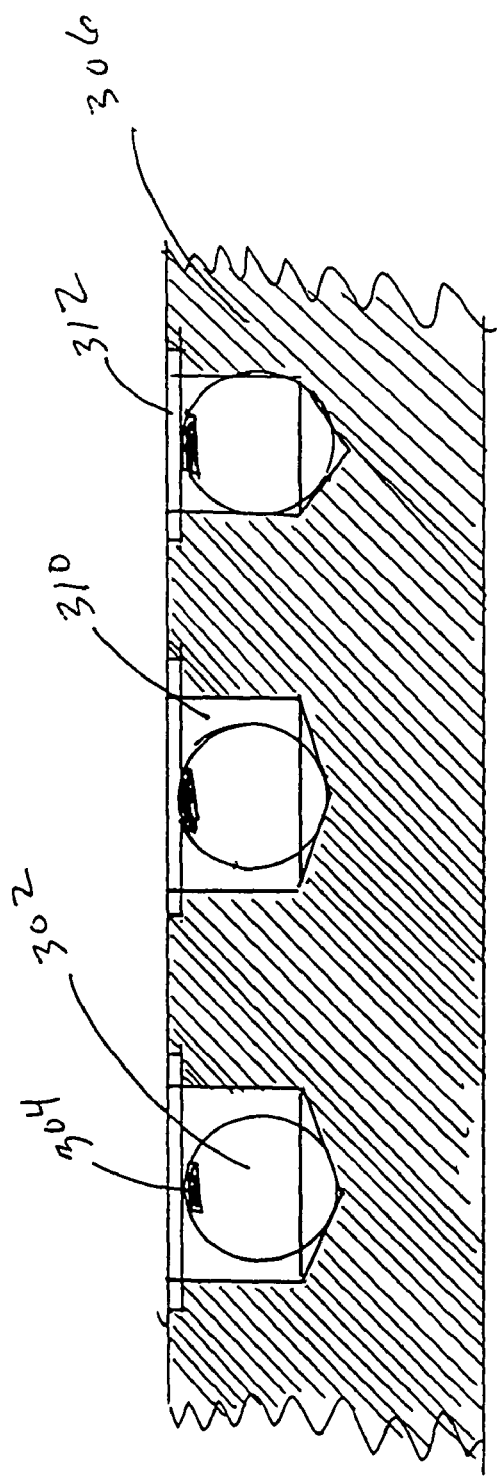

Referring to FIG. 3a, a long length of oligomode fiber optic waveguide 302 with a series of evanescent wave decouplers 304 is laid out on or incorporated into floor 306 of a barn or other live animal storage facility. At timed intervals, coherent light source 308, which is connected to fiber 302, is turned on and animals (not shown) are exposed to the radiation. This will increase the fertility of the animals as well as accelerate their growth. FIG. 3b depicts a cross section of waveguide 302 incorporated into floor 306. The waveguides 302 with evanescent decouplers 304 are placed in small channels 310 in the surface of floor 306. Windows 312 may be used to cover channels 310 to protect waveguides 302 therein.

EXAMPLE 4

Figure 4:
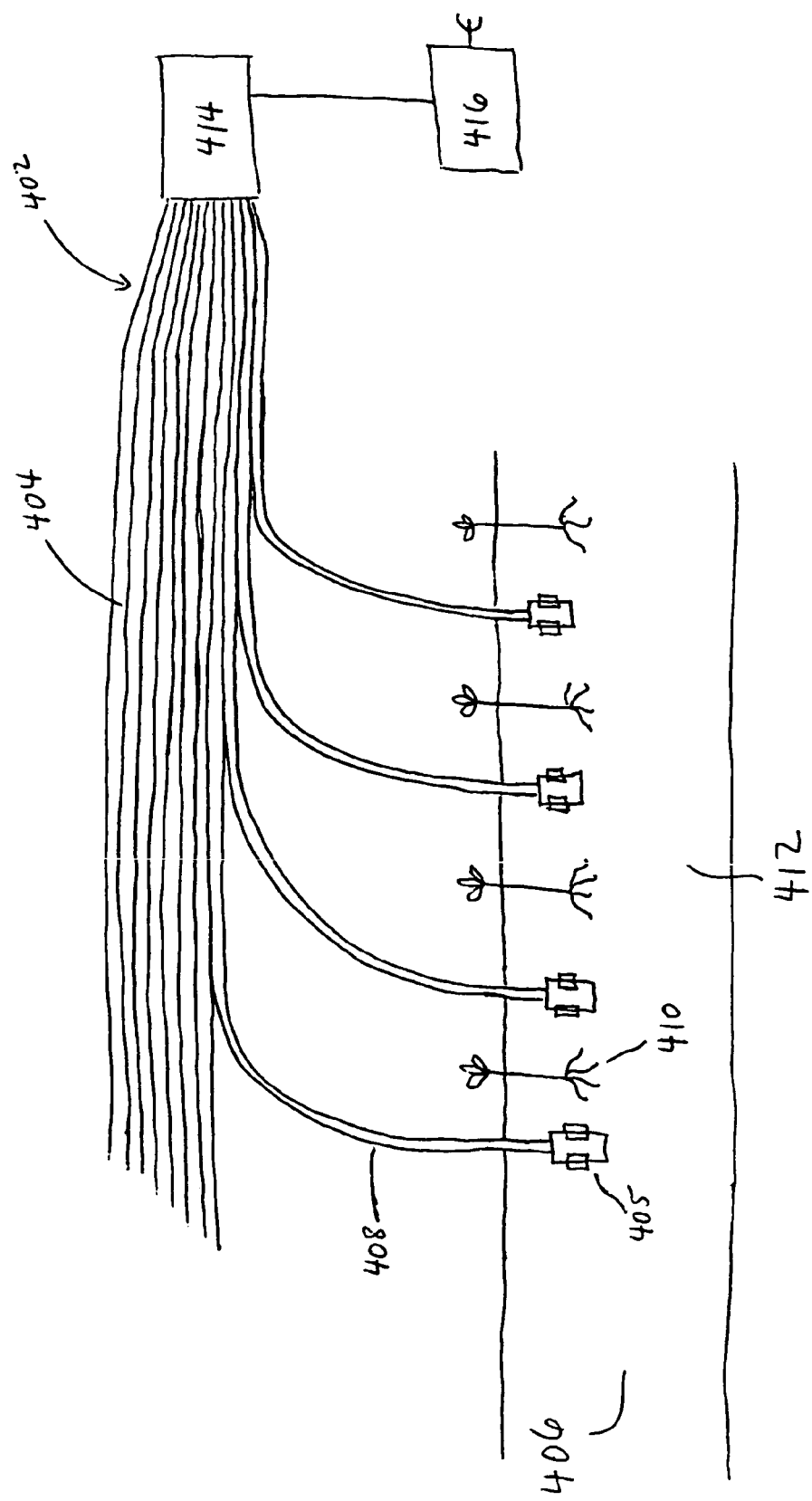
FIG. 4 illustrates a bundle of oligomode waveguides, branching off to provide targeted biostimulation.

Referring to FIG. 4, large bundle 402 of oligomode fibers 404 is brought across a field 406. At desired intervals individual fibers 408 are directed out from bundle 402 and placed along with seedling 410 into soil 412. Coherent light source 414 attached to bundle 402 transmits coherent light through fibers 404. Evanescent decouplers 405 leak radiation from fibers 404 to the nearby seedlings and soil. By controlling light source 414 with timer 416 seedlings 410 can be intermittently or constantly exposed to the biostimulating radiation.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method of biostimulation of organic tissue which is for enhancing growth of seedlings, comprising the steps of:
   a) choosing an oligomode transmission fiber having at least one means to selectively leak radiation from at least one preselected position along the length of said fiber, thus providing a laterally leaking fiber;
   b) placing said laterally leaking, oligomode transmission fiber in close proximity to said organic tissue at a plurality desired treatment sites, and wherein said means to selectively leak radiation are positioned so as to align lateral leaks at said desired treatment sites;
   c) activating a coherent light source at a proximal end of said fiber; and
   d) selectively leaking radiation from said source through said at least one means to selectively leak radiation from multiple positions along a length of said fiber independent from emission at a distal end; and
   wherein said steps comprising said method are more specifically:
      a1) assembling a bundle of said laterally leaking oligomode fibers of a length sufficient to traverse a planting area;
      b1) locating said bundle of laterally leaking oligomode fibers across said planting area,
      c1) directing individual laterally leaking oligomode fibers out of said bundle at desired planting intervals, said individual laterally leaking fibers having said means to selectively leak radiation from said individual oligomode fibers;
      d1) placing said lateral leaking individual fiber along with a seedling into the soil: and
      e1) transmitting coherent light from a light source through said laterally leaking oligomode fibers to deliver biostimulating radiation to said seedlings.

2. The method of claim 1 wherein step a is accomplished by choosing a cladded waveguide, which can selectively leak radiation along said length of fiber.

3. The method of claim 1 wherein step d is accomplished by selectively leaking radiation through evanescent wave decouplers positioned along preselected positions along said length of fiber.

4. The method of claim 1 wherein said irradiation according to step c is continuous.

5. A method of biostimulation of organic tissue, which is for enhancing seed germination and growth, comprising the steps of:
   a) choosing an oligomode transmission fiber having at least one means to selectively leak radiation from at least one preselected position along the length of said fiber, thus providing a laterally leaking fiber;
   b) placing said laterally leaking, oligomode transmission fiber in close proximity to said organic tissue at a plurality desired treatment sites, and wherein said means to selectively leak radiation are positioned so as to align lateral leaks at said desired treatment sites;
   c) activating a coherent light source at a proximal end of said fiber; and
   d) selectively leaking radiation from said source through said at least one means to selectively leak radiation from multiple positions along a length of said fiber independent from emission at a distal end; and
   wherein said steps comprising said method are more specifically:
      a1) selecting said laterally leaking oligomode fiber capable of transmitting a chosen wavelength for biostimulation;
      b1) placing said means to selectively leak radiation from said laterally leaking oligomode fiber at a desired planting interval along said fiber;
      c1) placing a length of said laterally leaking oligomode fiber along side seeds below grade during planting;

d1) transmitting coherent light from said light source through said laterally leaking oligomode fiber to deliver biostimulating radiation to said seeds.

6. The method of claim 5 wherein step a is accomplished by choosing a cladded waveguide, which can selectively leak radiation along said length of fiber.

7. The method of claim 5 wherein step d is accomplished by selectively leaking radiation through evanescent wave decouplers positioned along preselected positions along said length of fiber.

8. The method of claim 5 wherein said irradiation according to step c is continuous.

* * * * *